US006541429B2

(12) United States Patent
McConnachie et al.

(10) Patent No.: US 6,541,429 B2
(45) Date of Patent: Apr. 1, 2003

(54) LUBRICANT COMPOSITIONS

(75) Inventors: Jonathan M. McConnachie, Flemington, NJ (US); Ian A.W. Bell, Southmoor (GB); Alisdair J. Brown, Chilton (GB); Edward I. Stiefel, Bridgewater, NJ (US); Ernestine W. Hill, Piscataway, NJ (US)

(73) Assignee: Infineum International Ltd. (GB)

( * ) Notice: Subject to any disclaimer, the term of this patent is extended or adjusted under 35 U.S.C. 154(b) by 0 days.

(21) Appl. No.: 09/815,850

(22) Filed: Mar. 23, 2001

(65) Prior Publication Data

US 2001/0056043 A1 Dec. 27, 2001

(30) Foreign Application Priority Data

Mar. 29, 2000 (EP) .............................. 00201137

(51) Int. Cl.[7] ................... C10M 133/00; C10M 137/00; C10M 139/00
(52) U.S. Cl. ....................... 508/363; 508/379
(58) Field of Search ......................... 508/363

(56) References Cited

U.S. PATENT DOCUMENTS

| 3,419,589 A | 12/1968 | Larson et al. ............... 260/429 |
| 4,995,996 A | 2/1991 | Coyle et al. ............... 252/42.7 |
| 5,627,146 A | 5/1997 | Tanaka et al. .............. 508/363 |
| 5,824,627 A | * 10/1998 | McConnachie et al. ..... 508/363 |
| 5,837,657 A | 11/1998 | Fang et al. ................. 508/363 |
| 5,888,945 A | 3/1999 | Stiefel et al. ............... 508/363 |
| 5,906,968 A | * 5/1999 | McConnachie et al. ..... 508/363 |
| 6,110,878 A | * 8/2000 | McConnachie et al. ..... 508/363 |
| 6,143,701 A | * 11/2000 | Boffa ......................... 508/363 |
| 6,172,013 B1 | * 1/2001 | Holt et al. .................. 508/364 |
| 6,232,276 B1 | * 5/2001 | Stiefel et al. ............... 508/363 |

FOREIGN PATENT DOCUMENTS

| WO | WO98/26030 | 6/1998 | ........ C10M/159/18 |
| WO | WO99/47629 | 9/1999 | ........ C10M/159/00 |
| WO | WO99/66013 | 12/1999 | ........ C10M/159/18 |

OTHER PUBLICATIONS

"Preparation of Complexes Containing the $[Mo_3S(S_2)_3]^{4+}$ Core and Structure of Tris(diethyldithiocarbamato)tris($\mu_3$–thio)–triangulo–trimolybdenum(IV) Iodine", Zimmerman et al., Inorg. Chem. 1991, 30, 4336–4341.

* cited by examiner

Primary Examiner—Ellen M. McAvoy

(57) ABSTRACT

A lubricating oil composition is provided comprising a major amount of an oil of lubricating viscosity and a minor amount of, as an additive, at least one compound comprising a polynuclear molybdenum core and bonded thereto one or more anionic ligands capable of rendering the compound oil-soluble or oil-dispersible, wherein the ratio of the number of molybdenum atoms in the core to the number of said ligands is 1:1, such as 3:2 or greater.

13 Claims, No Drawings

LUBRICANT COMPOSITIONS

FIELD OF THE INVENTION

The present invention relates to lubricating oil compositions and concentrates therefor containing metal core compounds, specifically polynuclear molybdenum core compounds.

BACKGROUND OF THE INVENTION

Certain oil-soluble or oil-dispersible metal core compounds, ie compounds having a metal core bonded to one or more ligands, are known as additives (or additive components) for lubricating oil compositions (or lubricants) for improving the composition's properties and performance. The ligand or ligands confer oil-solubility on the compound. For example, certain oil-soluble molybdenum- and sulfur-containing compounds have been proposed and investigated as lubricant additives. U.S. Pat. Nos. 2,951,040; 3,419,589; 3,840,463; 4,966,719; 4,995,996; and 4,978,464 are representative of patent specifications describing molybdenum- and sulfur- containing compounds.

Molybdenum compounds for use as lubricant additives described in the art are principally dinuclear molybdenum compounds, characterised by the oxidation state Mo(V). See, for example, U.S. Pat. No. 5,627,146. Also, EP-A-0 960 178, based on International Patent Application No. PCT IB97/01656, describes use of trinuclear molybdenum compounds as lubricant additives, i.e. characterised by a different oxidation state (Mo(IV)).

Such dinuclear molybdenum compounds may be exemplified by the formula $Mo_2O_xS_yL_2$, and such trinuclear molybdenum compounds may be exemplified by the formula $MO_3S_kL_4$, where x+y=4, k is at least 4, and L represents a monoanionic ligand for conferring oil-solubility or oil-dispersability on the compound, a typical example being a dithiocarbamate, frequently referred to as "dtc".

The above-exemplified compounds have Mo: ligand (L) molar ratios of 1:1 and 3:4 respectively, ie the number of moles of Mo never exceeds the number of moles of ligand L. Since the Mo is an active part of the compound, it would be desirable to increase its proportion, relative to ligand L, in order to reduce the raw material cost of making the compounds. The art does not describe any such accomplishment, even though it would be beneficial to do so.

The present invention solves the above problem and provides oil-soluble or -dispersible compounds with polynuclear Mo cores whose Mo content exceeds its solubility or dispersibility conferring ligand content.

SUMMARY OF THE INVENTION

In a first aspect, the invention is a lubricating oil composition comprising, or made by mixing, a major amount of an oil of lubricating viscosity and a minor amount of, as an additive, at least one compound comprising a polynuclear, such as a di- or trinuclear, molybdenum core and bonded thereto one or more monoanionic ligands capable of rendering the compound oil-soluble or oil-dispersible, wherein the ratio of the number of molybdenum atoms in the core to the number of said ligands is greater than 1:1, such as 3:2 or greater. The compound may provide at least 1, for example 1 to 2000, such as 5 to 1000, preferably 20 to 1000, ppm by mass of the Mo, expressed as Mo atoms, based on the mass of the composition.

Preferably, the molybdenum core, as a Mo cluster core comprising more than one Mo atom, is dinuclear or trinuclear. It may contain non-metallic atoms consisting wholly or partly of sulphur. Preferably it consists of trinuclear molybdenum and sulphur. The ligands or ligands may, for example, be bidentate ligands, e.g. bonding to the core through two sulphur atoms.

The lubricating oil composition according to the first aspect of the invention has excellent antiwear, antioxidant, and friction-reducing properties; also it may be compatible with other additives used in formulating commercial lubricating oil compositions and can be made from readily available starting materials.

In a second aspect, the invention is an additive concentrate for blending with an oil of lubricating viscosity comprising, or made by mixing, an oleaginous carrier and from 1 to 200,000, for example 50 to 150,00, such as 50 to 100,000, ppm by mass of the Mo, expressed as Mo atoms, of an additive defined in the first aspect of the invention, based on the mass of the concentrate.

In a third aspect, the invention is a method of lubricating an internal combustion engine comprising operating the engine and lubricating the engine with a lubricating oil composition of the first aspect of the invention.

In a fourth aspect, the invention is use of an additive as defined in the first aspect of the invention for enhancing one or more lubricating oil properties of a lubricating oil composition.

In a fifth aspect, the invention is a method of making a lubricating oil composition or an additive concentrate comprising mixing an additive defined in the first aspect of the invention with an oil of lubricating viscosity or an oleaginous carrier.

In this specification:

"comprising" or any cognate word is taken to specify the presence of stated features, integers, steps or components, but does not preclude the presence or addition of one or more other features, integers, steps, components or groups thereof;

"major amount" means in excess of 50 mass % of the composition;

"minor amount" means less than 50 mass % of the composition, both in respect of the stated additive and in respect of the total mass % of all of the additives present in the composition, reckoned as active ingredient of the additive or additives;

the invention also provides the product obtained or obtainable as a result of any reaction between the various additive components of the composition or concentrates, essential as well as customary and optimal, under the conditions of formulation, storage or use;

"oil-soluble" or "dispersible" used herein do not necessarily indicate that the compounds or additives are soluble, dissolvable, miscible, or capable of being suspended in the oil in all proportions. These do mean, however, that they are, for instance, soluble or stably dispersible in oil to an extent sufficient to exert their intended effect in the environment in which the oil is employed. Moreover, the additional incorporation of other additives may also permit incorporation of higher levels of a particular additive, if desired.

DETAILED DESCRIPTION OF THE INVENTION

OIL OF LUBRICATING COMPOSITION

This oil may be selected from vegetable, animal, mineral, or synthetic oils. The oils may range in viscosity from light distillate mineral oils to heavy lubricating oils such as gas engine oil, mineral lubricating oil, motor vehicle oil, and heavy duty diesel oil. The oils may be unrefined, refined, and re-refined. The oil may be used oil.

The ligands, including ligands L, may be independently selected from the group of:

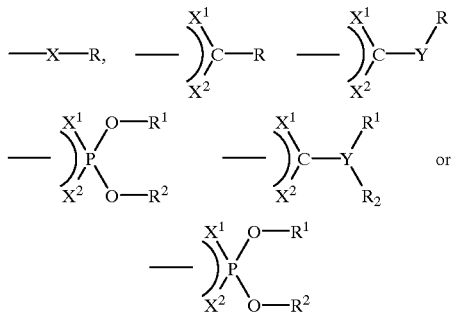

and mixtures thereof, and perthio derivatives thereof wherein X, $X_1$, $X_2$ and Y are independently selected from the group of oxygen and sulfur, and wherein $R_1$, $R_2$, and R are independently selected from the group consisting of H and organo groups that may be the same or different. Preferably the organo groups are hydrocarbyl groups such as alkyl (e.g., in which the carbon atom attached to the remainder of the ligand is primary, secondary or tertiary), aryl, substituted aryl and ether groups. More preferably, all ligands are the same.

Importantly, the organo groups of the ligands have a sufficient number of carbon atoms to render the compounds soluble or dispersible in the oil. The compounds' oil solubility or dispersibility may be influenced by the number of carbon atoms in the ligands. Preferably the ligand source chosen has a sufficient number of carbon atoms to render the compound soluble or dispersible in the oil. In the compounds in the present invention, the total number of carbon atoms present among all of the organo groups of the compounds' ligands typically will be at least 21, e.g. 21 to 800, such as at least 25, at least 30 or at least 35. For example, the number of carbon atoms in each alkyl group will generally range between 1 to 100, preferably 1 to 40 and more preferably between 3 and 20. Preferred ligands include dialkyldithiophosphate ("ddp"), xanthates, thioxanthates, dialkylphosphate, dialkyldithiocarbamate ("dtc"), and carboxylate and of these the dtc is more preferred.

The term "hydrocarbyl" denotes a substituent having carbon atoms directly attached to the remainder of the ligand and which is predominantly hydrocarbyl in character within the context of this invention. Such substituents include the following: (1) hydrocarbon substituents, that is, aliphatic (for example alkyl or alkenyl), alicyclic (for example cycloalkyl or cycloalkenyl) substituents, aromatic-, aliphatic- and alicyclic-substituted aromatic nuclei, as well as cyclic substituents wherein the ring is completed through another portion of the ligand (that is, any two indicated substituents may together form an alicyclic group); (2) substituted hydrocarbon substituents, that is, those containing non-hydrocarbon groups which, in the context of this invention, do not alter the predominantly hydrocarbyl character of the substituent. Those skilled in the art will be aware of suitable groups (e.g., halo, (especially chloro and fluoro), amino, alkoxyl, mercapto, alkylmercapto, nitro, nitroso, sulfoxy, etc.); (3) hetero substituents, that is, substituents which, while predominantly hydrocarbon in character within the context of this invention, contain atoms other than carbon present in a chain or ring otherwise composed of carbon atoms.

The compounds may, for example have the general formula (I) below:

$$Mo_a E_k L_n X_b \quad (1)$$

wherein E represents O, S or Se, or a combination thereof

L represents monoanionic ligands that confers oil-solublility or -dispersibility on the compound;

X represents an anion bonded to the core above, to confer electrical neutrality to the compound;

a is 2, 3 or 4:

k is at least 4, for example in the range from 4 to 10, such as 4 to 7, preferably 4 or 7;

n is an integer that is less than a; and b is an integer to confer, in combination with n, electrical neutrality to the compound.

Preferred embodiments of compounds of formula (I) are those where E represents O or S or a combination thereof; and/or a is 2 or 3.

A more preferred embodiment is a compound of the general formula (II) below:

$$Mo_3 S_k L_2 X$$

where k is 4 or 7 and X (II) represents a divalent anion such as the disulfide ion.

The subject compounds may be made by reacting, in a polar medium, a reactant molybdenum compound that contains a polynuclear molybdenum core, such as a trinuclear molybdenum core, and the ligand, L, such as a dithiocarbamate, in a stoichiometric ratio, corresponding to that of the subject compound, wherein neither the reactant molybdenum compound nor the ligand is derivatised.

The polar medium may, for example, comprise a liquid alkanol such as methanol, tetrahydrofuran, dimethylformamide, toluene or water; the reactant molybdenum compound may, for example, contain the $[Mo_3S_{13}]^{2-}$ ion; and L may, for example, be a dihydrocarbyl-, preferably dialkyl-, substituted dithiocarbamate. Appropriately, the above-described reaction is conducted at elevated temperature.

By "stoichiometric ratio" above is not intended to mean or require exact stoichiometry according to a chemical equation that can be written to represent the reaction, but rather close enough to the stoichiometry of such equation to ensure that there is more Mo than ligand, L, in the product (mole: mole).

As an example, the synthesis of $MO_3S_7(dtc)_2$ $(S_2)$, being a subject compound, may proceed with stoichiometric quantities of dtc according to the equation shown below:

$$(NH_4)_2 Mo_3 S_{13} + 2Hdtc \rightarrow Mo_3 S_7 (dtc)_2 (S_2) + 2H_2 S_2 + 2NH_3$$

COMPOSITION AND CONCENTRATE

The lubricating oil compositions of the present invention may be prepared by adding to an oil of lubricating viscosity a mixture of an effective minor amount of at least one compound, and, if necessary, one or more co-additives such as described hereinafter. This preparation may be accomplished by adding the compound directly to the oil or by first mixing the compound in a suitable carrier fluid to achieve oil solubility or dispersibility, and adding the mixture to the lubricating oil. Co-additives may be added to the oil by any method known to those skilled in the art, either prior to, contemporaneously with, or subsequent to addition of the compound.

Concentrates of the compounds and co-additives, if required, in a suitable oleagenous, typically hydrocarbon, carrier fluid provide a convenient means of handling them before their use. Oils of lubricating viscosity, such as those described above as well as aliphatic, naphthenic, and aromatic hydrocarbons, are examples of suitable carriers for concentrates. These concentrates may contain 1 to 90 mass % of the additives based on the weight of the concentrate; preferred is 1 to 50, more preferably 20 to 70, mass %.

The lubricating oil compositions made by mixing (or blending) an oil of lubricating viscosity containing at least one compound of the types and in the amounts described herein and optional co-additives may be used to lubricate mechanical engine components, particularly of an internal combustion engine such as a spark-ignited or compression-ignition engine, by adding the lubricating oil thereto in the crankcase thereof.

CO-ADDITIVES

Other lubricant additives may be used for blending in the compositions of this invention. These include dispersants, detergents, e.g., single or mixed metal detergent systems, pour point depressants, viscosity improvers, antioxidants, surfactants, antiwear agents, and friction reducing agents. These can be combined in proportions known in the art. For example, additives containing phosphorus and/or sulfur compounds such as a zinc dialkyl dithiophosphate(ZDDP) can be prepared and used with the compounds of the present invention. However, the compounds of the present invention may be effective or may even possess improved properties when used in lubricating oil compositions that are free or substantially free of added phosphorus and/or sulfur. i.e., phosphorus and/or sulfur in addition to (i.e., except for) any phosphorus or sulfur contained in the compounds themselves. A lubricating oil composition that is substantially free of phosphorus and/or sulfur is one in which the amount of phosphorus and/or sulfur is not more than is inherently present in base oils of lubricating viscosity.

Particularly noteworthy is the use of anti-oxidants in combination with the compounds.

Examples of suitable antioxidants are selected from copper-containing antioxidants, sulfur-containing antioxidants, aromatic amine-containing antioxidants and phenolic antioxidants.

Examples of suitable copper-containing antioxidants include oil-soluble copper compounds described in EP-B-24 146, EP-A-280 579 and EP-A-280 580. Thus, for example, the copper may be blended into the oil as an oil-soluble copper salt of a synthetic or natural carboxylic acid. Examples of carboxylic acids from which suitable copper salts may be derived include $C_2$ to $C_{18}$ carboxylic acids (e.g., acetic acid, and fatty acids such as stearic acid and palmitic acid), unsaturated acids (e.g., oleic acid), branched carboxylic acids (e.g., naphthenic acids of molecular weight of from 200 to 500, neodecanoic acid and 2-ethylhexanoic acid), and alkyl- or alkenyl-substituted dicarboxylic acids (e.g., polyalkenyl-substituted succinic acids such as octadecenyl succinic acids, dodecenyl succinic acids and polyisobutenyl succinic acids). In some cases, suitable compounds may be derived from an acid anhydride, for example, from a substituted succinic anhydride. The copper antioxidant may be, for example, a copper dithiocarbamate or copper dithiophosphate. Other copper- and sulfur-containing antioxidant compounds, for example, copper mercaptides, xanthates, and thioxanthates, are also suitable for use in accordance with the invention, as are copper sulfonates, phenates (optionally sulfurized) and acetylacetonates. Other copper compounds which may be used in accordance with the invention are overbased copper compounds. Examples of such compounds, and of processes for their preparation, are described in U.S. Pat. No. 4,664,822 and EP-A-0 425 367. The copper compound may be in cuprous or cupric form.

Examples of suitable aromatic amine-containing antioxidants are aromatic amines which have at least one aromatic group directly attached to at least one amine nitrogen atom. Secondary aromatic amines, especially those having two aromatic groups attached to the same amine nitrogen atom, are preferred, but the use of other aromatic amines is not excluded. The amines may contain one or more aromatic groups, for example at least two aromatic groups. Where there are two aromatic groups, both are preferably bonded directly to the same amine nitrogen. Compounds in which two aromatic groups are linked by a covalent bond or by an atom or group (e.g., an oxygen or sulfur atom, or a —CO—, —$SO_2$— or alkylene group) may be used. Aromatic rings, which are preferably aromatic hydrocarbon rings, may be unsubstituted or substituted by one or more substituents selected from alkyl, cycloalkyl, alkoxy, aryloxy, acyl, acylamino, hydroxy, and nitro groups. Amines containing alkyl-substituted aromatic hydrocarbon rings are preferred, especially those containing two alkylsubstituted phenyl groups. Preferred N-aryl amines for use in accordance with the invention are naphthylamines and, especially, diphenylamines, including alkyl substituted diphenylamines, wherein the alkyl group may be the same or different, having 1 to 28 carbon atoms. Other nitrogen-containing antioxidants, for example, phenothiazine type compounds, may also be used in this invention.

Examples of phenolic antioxidants include (a) sterically hindered tertiary-alkylated monohydric phenols such as those described in more detail in U.S. Pat. Nos. 2,944,086; 3,043,775; and -3,211,652; and (b) methylene-bridged tertiary alkyl polyphenols, such as 4,4'-methylene bis (2,6-di-tertbutylphenol) and 2,2'-methylene bis (4,6-di-(1,1,2-trimethylpropyl)phenol), and mixtures of (a) and (b) such as those described in more detail in EP-B-0456925.

Examples of sulfur-containing antioxidants (compounds) are alkaline earth metal salts of alkylphenoithioesters having preferably C5 to C12 alkyl side chains, calcium nonylphenol sulfide, ashless oil-soluble phenates and sulfurized phenates, phosphosulfurized or sulfurized hydrocarbons, phosphorus esters and other sulfur-containing molybdenum-containing compounds. Other examples of sulfur-containing antioxidants are metal salts of dihydrocarbyl dithiophosphate or dihydrocarbyl dithiocarbamate compounds, wherein the metal is selected from Zn, Mn, Ni, Al, Group 1 metals and Group 2 metals. Other sulfur-containing compounds include those described in EP-A-699 759, for example, sulfides of oils, fats or polyolefins, in which a sulfur group having two or more sulfur atoms is adjoined and bonded together in a molecular structure. Examples include sulfurized sperm oil, sulfurized pinene oil, sulfurized soybean oil, sulfurized polyolefin, sulfurized esters, dialkyl disulfide, dialkyl polysulfide, dibenzyl disulfide, ditertiary butyl disulfide, polyolefin polysulfide, a thiadiazole type compound such as bis-alkyl polysulfide thiadiazole, and sulfurized phenol.

Preferable antioxidants are copper-containing antioxidants, aromatic amine-containing compounds including diphenylamines and derivatives thereof that have an effect herein comparable to diphenylamines), and mixtures thereof. Examples of copper-containing antioxidants include copper polyisobutylene succinic anhydride ("copper PIBSA") and copper oleate, and diphenylamines include all effective derivatives of diphenylamines.

Thus, the lubricating oil compositions of the present invention may include a minor amount of at least one antioxidant and at least one oil-soluble or oil-dispersible compound. The composition may include a mixture of the compounds and antioxidants of the types disclosed herein, the lubricating oil and/or other additives disclosed herein per se, and/or of any intermediates and reaction products occurring as a result of the mixture. In combination, the antioxidants and compounds are present in a minor effective amount to produce the enhanced lubricating performance, particularly friction reduction, friction reduction retention, antioxidancy and/or antiwear properties in the oil.

EXAMPLES

The invention will be more fully understood by reference to the following examples.

Example 1

Preparation of $Mo_3S_7(octyl_2dtc)_2(S_2)$

Methanol (50 mL), dioctylamine (0.66 mL, 2.2 mmol), and carbon disulfide (0.13 mL, 2.2 mmol) were combined in a 250 mL round bottomed flask under a nitrogen atmosphere and allowed to stir for 2 hours. $(NH_4)_2Mo_3S_{13}$ (750 mg, 1 mmol) was added and the mixture heated and refluxed overnight. The mixture, containing a red solid, was removed from the heat and the methanol decanted from the red solid. The solid was washed with methanol, dried, dissolved in toluene and filtered. The toluene was removed by vacuum distillation to yield a dark-red glassy solid product, whose elemental analysis corresponded to that of $Mo_3S_7(octyl_2dtc)_2(S_2)$.

Example 2

Preparation of $Mo_3S_7(coco_2dtc)_2(S_2)$:

Methanol (50 mL), dicocoamine (1.00 g, 2.2 mmol), and carbon disulfide (0.13 mL, 2.2 mmol) were combined in a 250 mL round bottom flask under nitrogen and allowed to stir for 2 h. $(NH_4)_2Mo_3S_{13}$ (750 mg, 1 mmol) was added to the solution. The mixture was heated and refluxed overnight. The solution was removed from heat and the methanol decanted from the red solid. The solid was washed with methanol and then dried. The product was dissolved in toluene and filtered. The toluene was removed via vacuum distillation to yield a dark-red glassy solid.

Test

The product of Example 2 was subjected to the Cameron-Plint test as follows.

It was added, as an additive, to a commercial 10W30 lubricating oil to provide 500 ppm by weight of elemental Mo. The mixture was heated at 80° C. for 30 minutes with vigorous stirring to disperse the additive. The untreated oil and the additive-containing oil were then subject to the Cameron-Plint ball-on-plate test, which provides a measure of friction modification. The conditions of the test were:

| Load | 120N |
|---|---|
| Stroke | 2.42 cm |
| Temperature | 120° C. |
| Rate | 8.3 Hz |

The length of the test was 30 minutes: the final friction coefficient was measured at the end of the test and the average friction coefficient recorded as the mean of the values between 10 and 30 minutes. The results obtained were as follows:

| | Final Friction Coefficient | Average Friction Coefficient |
|---|---|---|
| Untreated Oil | 0.10 | 0.11 |
| Treated Oil | 0.04 | 0.04 |

It is thus seen that treatment with the product of Example 2 reduced friction by more than half.

What is claimed is:

1. A lubricating oil composition comprising, or made by mixing, a major amount of an oil of lubricating viscosity and a minor amount of at least one compound comprising a polynuclear molybdenum core having bonded thereto one or more monoanionic ligands capable of rendering the compound oil-soluble or oil- dispersible, and at least one anionic group that is not a solubility or dispersibility conferring ligand, wherein the combination of said one or more monoanionic ligands and said at least one anionic group confers electical neutrality to the compound and wherein the ratio of the number of molybdenum atoms in the core to the number of said ligands is greater than 1:1.

2. The composition of claim 1 wherein the compound or compounds are represented by the general formula (I) below:

$$Mo_aE_kL_nX_b \qquad (I)$$

wherein E represents O, S or Se, or a combination thereof;
L represents a monoanionic ligand that confers oil-solublility or -dispersibility on the compound;
X represents an anion bonded to the core, other than L above, to confer electrical neutrality to the compound;
a is 2, 3 or 4:
k is at least 4;
n is an integer that is less than a; and
b is an integer to confer, in combination with n, electrical neutrality to the compound.

3. The composition of claim 2 wherein E represent O or S or a combination thereof, and/or a is 2 or 3.

4. The composition of claim 3 wherein the compound or compounds are represented by the general formula (II):

$$Mo_3S_kL_2X \qquad (II)$$

wherein k is 4 or 7, and X represents a divalent anion.

5. The composition of claim 1 wherein said ligand or ligands, including L, is or are represented by formulae

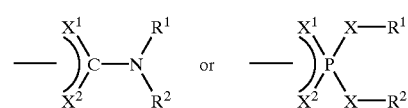

and mixtures thereof, and perthio derivatives thereof wherein X, $X^1$, $X^2$ and Y are independently selected from the group of oxygen and sulfur, and wherein $R^1$ and $R^2$ independently represent hydrocarbyl groups.

6. The composition of claim 5 wherein the or said ligand or ligands is a dialkyldithiophosphate or a dialkyldithiocarbamate ligand.

7. The composition of claim 1 wherein the mass of molybdenum from the compound is at least 1 ppm based on the mass of the composition.

8. The composition of claim 1 wherein the total number of carbon atoms in all of the ligands is at least 21.

9. The composition of claim 1 wherein the oil of lubricating viscosity is free of sulphur.

10. The composition of claim 1 further comprising, or made by mixing, at least one antioxidant additive.

11. The composition of claim 1 further comprising, or made by mixing, one or more dispersants, detergents, pour point depressants, viscosity improvers, surfactants and anti-wear agents.

12. An additive concentrate for blending with an oil of lubricating viscosity comprising, or made by mixing, an oleaginous carrier and from 1 to 200,000 ppm by mass of the molybdenum of an additive as defined in claim 1, based on the mass of the concentrate.

13. An additive concentrate of claim 12 further comprising, or made by mixing, at least one antioxidant additive, whereby the concentrate contains from 1 to 90, mass percent of additives based on the mass of the concentrate.

* * * * *